United States Patent
Wallace

(10) Patent No.: US 11,672,688 B2
(45) Date of Patent: Jun. 13, 2023

(54) ADJUSTABLE NASAL DILATOR

(71) Applicant: Nasal Dilator LLC, Hartford, CT (US)

(72) Inventor: Tom Wallace, Durham, CT (US)

(73) Assignee: NASAL DILATOR LLC, Hartford, CT (US)

( * ) Notice: Subject to any disclaimer, the term of this patent is extended or adjusted under 35 U.S.C. 154(b) by 308 days.

(21) Appl. No.: 16/855,545

(22) Filed: Apr. 22, 2020

(65) Prior Publication Data

US 2020/0337877 A1 Oct. 29, 2020

Related U.S. Application Data

(60) Provisional application No. 62/837,465, filed on Apr. 23, 2019.

(51) Int. Cl.
*A61F 5/08* (2006.01)

(52) U.S. Cl.
CPC ...................... *A61F 5/08* (2013.01)

(58) Field of Classification Search
CPC . A61F 5/08; A61F 5/56; A61M 15/08; A61M 15/085; A61M 15/002; A61M 2210/0618
See application file for complete search history.

(56) References Cited

U.S. PATENT DOCUMENTS

| | | | |
|---|---|---|---|
| 5,816,241 A | 10/1998 | Cook | |
| 5,989,270 A * | 11/1999 | Suh | A61F 5/08 606/157 |
| 6,238,411 B1 | 5/2001 | Thorner | |
| 6,863,066 B2 | 3/2005 | Ogle | |
| 7,105,008 B2 | 9/2006 | Maryanka | |
| 8,834,512 B1 | 9/2014 | Brown et al. | |
| 2010/0063532 A1* | 3/2010 | Moore | A61F 5/56 606/199 |
| 2013/0157810 A1* | 6/2013 | McDevitt | A63B 21/0004 482/13 |
| 2015/0173934 A1* | 6/2015 | Castillo | A61F 5/08 606/204.45 |

* cited by examiner

*Primary Examiner* — Majid Jamialahmadi
(74) *Attorney, Agent, or Firm* — Cantor Colburn LLP

(57) ABSTRACT

A nasal dilator includes a first leg and a second leg insertable into a pair of respective nasal openings. The first leg and the second leg are separated by a clearance. A connecting member extends between the first leg and the second leg and an adjustment mechanism is operably coupled to both the first leg and the second leg. The adjustment mechanism includes a tension shaft that is rotatable about an axis to vary the clearance.

14 Claims, 2 Drawing Sheets

ADJUSTABLE NASAL DILATOR

CROSS-REFERENCE TO RELATED APPLICATIONS

This US non-provisional application claims priority to U.S. Ser. No. 62/837,465, which was filed on Apr. 23, 2019, the contents of which are incorporated herein by reference.

BACKGROUND

Embodiments of the present disclosure relate generally to a cooking system, and more particularly, to a guard for blocking a flow of fat or oil from contacting a heating element of a cooking system.

Every year millions of individuals spray chemicals into their nostrils and attach devices to their noses in an attempt to improve nasal breathing. A large percentage of the human population experiences periodic nasal air passage restrictions resulting from sinus irritations, changes in barometric pressure, nasal structure and other causes. This condition is particularly bothersome at night and often causes poor air filtration, disrupted sleep patterns, excessive breathing through the mouth, dry mouth, snoring, and other discomforts and health problems.

SUMMARY

According to an embodiment, a nasal dilator includes a first leg and a second leg insertable into a pair of respective nasal openings. The first leg and the second leg are separated by a clearance. A connecting member extends between the first leg and the second leg and an adjustment mechanism is operably coupled to both the first leg and the second leg. The adjustment mechanism includes a tension shaft that is rotatable about an axis to vary the clearance.

In addition to one or more of the features described above, or as an alternative, in further embodiments the tension shaft is threadably coupled to at least one of the first leg and the second leg.

In addition to one or more of the features described above, or as an alternative, in further embodiments lateral movement of the tension shaft is restricted relative to the body.

In addition to one or more of the features described above, or as an alternative, in further embodiments the tension shaft includes a head arranged at a first end and a nut arranged at a second end, the head being located adjacent an first surface of the body and the nut being arranged adjacent a second, opposite side of the body.

In addition to one or more of the features described above, or as an alternative, in further embodiments a first through opening is formed in the first leg and a second through opening is formed in the second leg and the tension shaft extends through both the first through opening and the second opening.

In addition to one or more of the features described above, or as an alternative, in further embodiments the second through opening is threaded.

In addition to one or more of the features described above, or as an alternative, in further embodiments at least one of the first leg and the second leg is formed from a high flexure material.

In addition to one or more of the features described above, or as an alternative, in further embodiments the connecting member is formed from a medium flexure material.

In addition to one or more of the features described above, or as an alternative, in further embodiments the first leg, the second leg, and the connecting member are integrally formed.

In addition to one or more of the features described above, or as an alternative, in further embodiments a first contact region is formed at an exterior surface of the first leg and a second contact region is formed at an exterior surface of the second leg.

In addition to one or more of the features described above, or as an alternative, in further embodiments at least one of the first contact region and the second contact region includes a contoured surface for gripping a nasal surface.

In addition to one or more of the features described above, or as an alternative, in further embodiments each of the first contact region and the second contact region is formed by a pad mounted to a distal end of the first leg and the second leg, respectively.

In addition to one or more of the features described above, or as an alternative, in further embodiments at least a portion of the body is coated with a layer of soft material.

BRIEF DESCRIPTION OF THE FIGURES

The accompanying drawings incorporated in and forming a part of the specification embodies several aspects of the present disclosure and, together with the description, serves to explain the principles of the disclosure. In the drawings.

The detailed description explains embodiments of the disclosure, together with advantages and features, by way of example with reference to the drawings.

DETAILED DESCRIPTION

Figure 1:
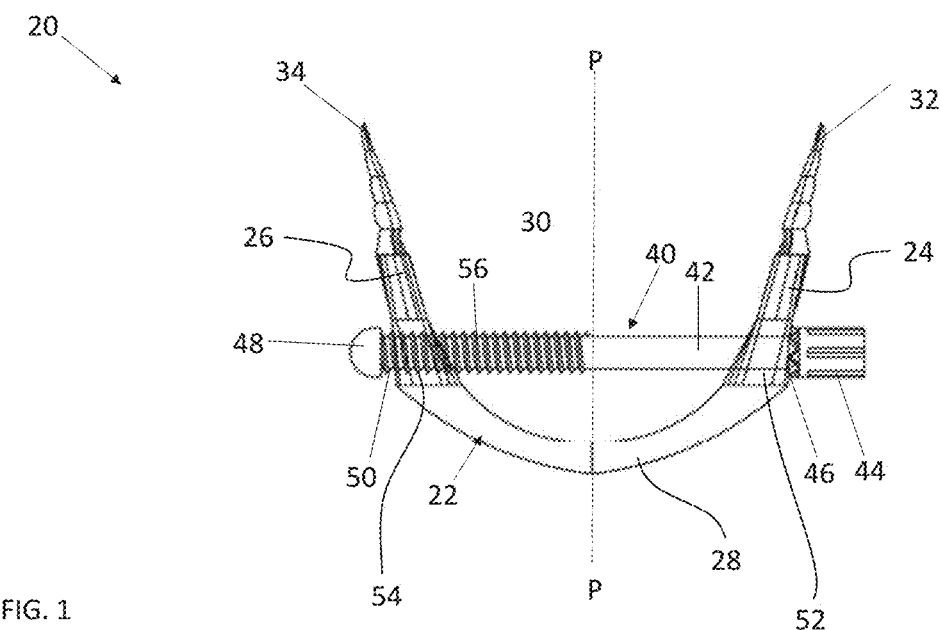
FIG. 1 is a schematic view of a nasal dilator according to an embodiment.
Figure 2:
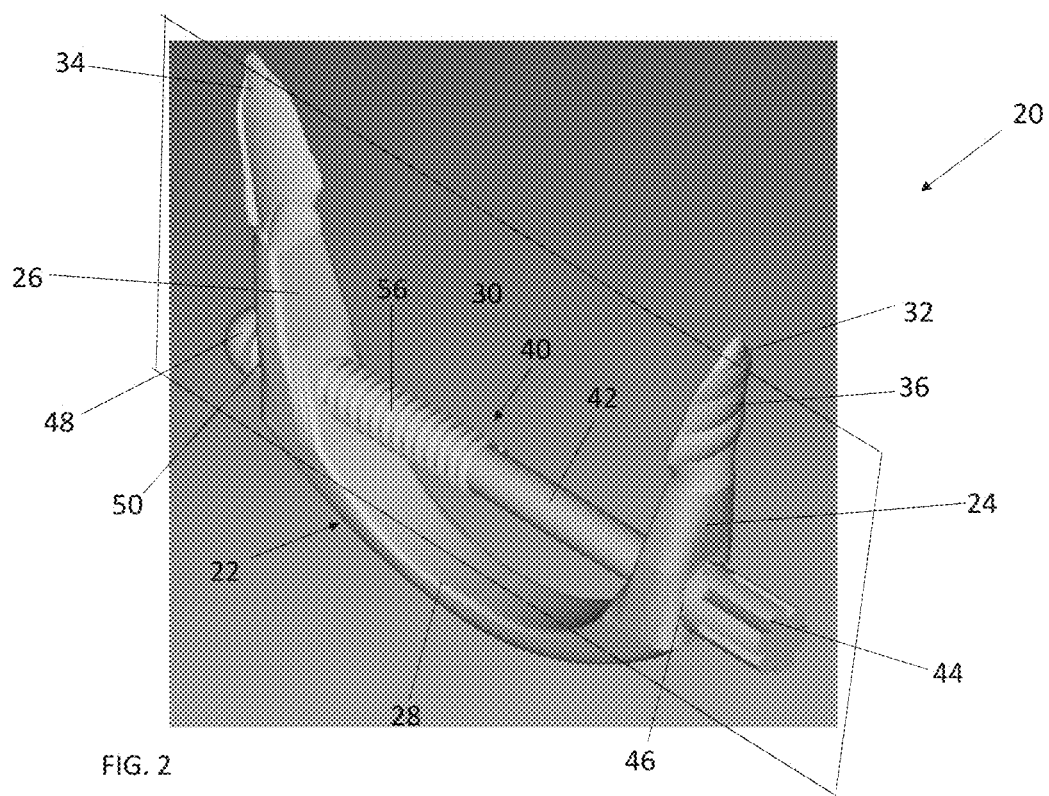
FIG. 2 is a perspective view of a nasal dilator according to an embodiment.

With reference now to FIGS. 1 and 2, an example of a nasal dilator 20 according to an embodiment is illustrated. As shown, the nasal dilator 20 includes a body 22 having a first leg 24 and a second leg 26. An arcuate connecting member 28 extends between a first end of both the first leg 24 and the second leg 26 to form a body 22 having an approximate U-shape or C-shape. In the illustrated, non-limiting embodiment, the first leg 24, the connecting member 28, and the second leg 26 are integrally formed from a single piece of material. However, it should be understood that embodiments where the body 22 is formed from multiple pieces that are connected, such as welded together for example, are also within the scope of the disclosure.

The first leg 24 and the second leg 26 may be substantially identical such that the body 22 is generally symmetrical about a central plane P extending through the gap 30 defined between the first leg 24, the connecting member 28, and the second leg 26. The first leg 24 and the second leg 26 may also be symmetrical about a plane S extending through a center of the first leg 24, the connecting member 28, and the second leg 26. In such embodiments, the nasal dilator 20 may be properly installed within a nose in either a first configuration, or alternatively, in a second configuration, the second configuration being rotated 180 degrees relative to the first configuration. Embodiments where the first leg 24 and the second leg 26 have different configurations and/or embodiments where an upper surface and a lower surface of a leg 24, 26 have different configurations are also contemplated herein.

In an embodiment, a thickness of each of the first leg 24 and the second leg 26 is greatest at the first end, adjacent the interface with the connecting member 28. From this interface, the thickness of each leg 24, 26 may gradually reduce towards a second distal end 32, 34, respectively, such as for ease of insertion into a nostril.

A contact region 36 is located at the distal end 32, 34 of each leg 24, 26. The contact region 36 includes the portion of each leg 24, 26 that is receivable within a nostril and that is configured to directly contact an interior surface of the nostril when the nasal dilator 20 is installed. As shown, the contact region 36 is defined at an exterior surface of each leg 24, 26. In an embodiment, the contact region 36 is contoured to maximize comfort to a user while also limiting slippage of the nasal dilator 20 relative to the nostril at the contact region 36. For example, the illustrated contact region 36 includes a plurality of rounded ridges operable to grip a corresponding interior surface of a user's nostril. However, any suitable configuration or contour of the contact region 36 is within the scope of the disclosure. In an embodiment, the contact region 36 may be formed by a pad removably or permanently mounted to a portion of the leg 24, 26, such as in overlapping relationship with the distal end 32, 34 of each leg 24, 26 for example. In other embodiments, the contour of the contact region 36 may be formed directly into the material of the leg 24, 26 itself.

The body 22 of the nasal dilator 20 may be formed from any suitable material, including a plastic, metal, or composite material for example. In an embodiment, the body 22 is formed from a resilient material that allows at least one of the first leg 24 and the second leg 26 to flex or bend for insertion into a nasal cavity. For example, at least a portion of the first leg 24 and the second leg 26 may be formed using a material having a high flexural strength and the connecting member 28 may be formed from a material having a reduced, medium flexural strength. However, embodiments where both the legs 24, 26 and the connecting member 28 are formed from the same material, such as a high flexural strength material, or alternatively, from a medium flexural strength material are also contemplated herein. Further, in an embodiment, all or a portion of the body 22, such as the distal ends 32, 34 of the legs 24, 26, including the contact region 36 for example, may be coated with a thin layer of soft material, such as with a urethane or silicon for example.

The nasal dilator 20 may be adjustable to accommodate use in different size nasal cavities. More specifically, the distance between the distal end 32 of the first leg 24 and the distal end 34 of the second leg 26 may be varied. As shown in the FIGS., the nasal dilator 20 additionally includes an adjustment mechanism 40 operable to adjust the configuration of the body 22. In the illustrated, non-limiting embodiment, the adjustment mechanism 40 is a tension control rod. The tension control rod 40 includes a shaft 42 having a cap or head 44 located at the first end 46 of the shaft 42 and a nut 48 located at the second, opposite end 50 of the shaft 42. A first through opening 52 is formed near the first end of the first leg 32, adjacent the interface with the connecting member 28, and a second through opening 54 is formed near the first end of the second leg 26, adjacent the interface with the connecting member 28. The shaft 42 extends through the first through opening 52 and the second through opening 54 such that the head 44 of the tension control rod 40 is disposed generally adjacent an exterior surface of the first leg 24 and the nut 48 of the tension control rod 40 is located generally adjacent an exterior surface of the second leg 26. In an embodiment, the portion of the body 22 through which the first through opening 52 and the second through opening 54 are formed is more rigid than the distal ends 32, 34 of the legs 24, 26.

The tension control rod 40 cooperates with the first through opening 52 and the second through opening 54 to selectively apply a force to the first and second legs 24, 26 to transform the first and second leg 24, 26 between a normal, fully open position (FIG. 1), and a partially closed or retracted position (not shown). In the illustrated, non-limiting embodiment, at least a portion 56 of the shaft 42 of the tension control rod 40 includes a plurality of threads, and the second through opening 54 includes a plurality of threads complementary to the threads of the shaft 42. However, embodiments where both the first through opening 52 and the second through opening 54 are threaded are also within the scope of the disclosure.

A user may apply a rotational force to the tension control rod 40, such as via the head 44 for example, to adjust the configuration of the nasal dilator 20. As the tension control rod 40 is rotated about its axis X in a first direction, the threaded engagement between the second through opening 54 and the threaded portion 56 of the shaft 42 applies a force to the second leg 26 of the body 22. Because lateral movement of the shaft 42 relative to the first leg 24 is restricted by the head 44, this rotation causes the second leg 26 to move towards the first leg 24, resulting in a clearance between the nut 48 and the adjacent surface of the leg 26. Because of the resilience or flexure of the material of the leg 26 and the connecting member 28, the leg 26 and/or the connecting member 28 is configured to bend in response to the force, thereby reducing the distance between the distal ends 32, 34 of the legs 24, 26.

When the tension control rod 40 is rotated in a second, opposite direction about the axis X, the resiliency of the material of the legs 24, 26 and connecting member 28, causes the body 22 to bias towards the normal, extended position. The bias of the leg 26 is restricted only by threaded engagement with the shaft 42 and the nut 48. The adjustment mechanism 40 illustrated and described herein is intended as an example only, and it should be understood that other suitable mechanisms for controlling the distance between the distal ends 32, 34 of the legs 24, 26 is within the scope of the disclosure.

To use the nasal dilator 20, an operator may operate the adjustment mechanism 40 until the distal ends of the legs 24, 26 are separated by a distance such that each end 32, 34 is receivable within a corresponding nostril of a user's nose. Once the end 32, 34 of each leg 24, 26 is positioned within a nostril, the adjustment mechanism 40 may be further operated to affix the nasal dilator 20 to the nose. For example, in an embodiment, the distance between the legs 24, 26 may be adjusted to control the pressure applied by the legs 24, 26 to a corresponding portion of the nose, while maintaining a level of comfort experienced by the wearer.

When installed into the nostrils and affixed in an operating position, the contact region 36 of each leg 24, 26 is arranged in contact with the tissue arranged at the interior surface of the outer wall of each nostril. The nasal dilator 20 does not contact the septum or septal cartilage when affixed in an operating position. In an embodiment, the legs 24, 26 are positionable just inside the nasal openings, in what is referred to as the vestibule of the nose. However, embodiments where the nasal dilator 20 extends beyond the vestibule of the nose are also contemplated herein.

The pressure applied by the legs 24, 26 to the interior surface of the outer wall of each nostril is suitable to expand the opening of the nostril (i.e. nasal passage) formed between the septum and the outer wall of each nostril. The magnitude of the force is a function of the distance between the distal ends 32, 34 of the legs 24, 26 of the nasal dilator 20. In an embodiment, the force applied by the legs 24, 26, to a surface of a nostril not only opens the nasal passages, but also, may adjust the geometry of the flow area of each nasal passage. This pressure applied by the legs 24, 26 to the outer walls of the nostril opens the nasal passages, thereby maximizing the volume of air that can flow into and out of the nose. Further, because the nasal dilator 20 is only arranged in direct contact with the interior surface of the outer wall of each nostril, and not with the interior walls of the nose, the invasiveness of the dilator 20 is minimized, resulting in improved comfortability to the user while the flow through the nasal passages is maximized.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Exemplary embodiments of this disclosure are described herein, including the best mode known to the inventors for carrying out the disclosure. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A nasal dilator comprising:
   a first leg and a second leg insertable into a pair of respective nasal openings, the first leg and the second leg being separated by a clearance and each of the first and second legs having a first end and a second end, an outwardly facing surface of each of the first end of the first and second legs including a contact region configured to contact an interior surface of a nostril, wherein the first leg and the second leg are movable between an extended position and a retracted position, wherein the first leg and the second leg are integrally formed from a resilient material having a bias toward the extended position and a thickness of at least one of the first leg and the second leg tapers from the second end towards the first end;
   a connecting member extending between the first leg and the second leg; and
   an adjustment mechanism operably coupled to both the first leg and the second leg, wherein the adjustment mechanism includes a tension shaft that is rotatable about an axis to oppose the bias of the first and second legs towards the extended position and control an outward pressure configured to be applied to each nostril.

2. The nasal dilator of claim 1, wherein the tension shaft is threadably coupled to at least one of the first leg and the second leg.

3. The nasal dilator of claim 2, wherein the first and second legs in combination with the connecting member form a body, wherein lateral movement of the tension shaft is restricted relative to the body.

4. The nasal dilator of claim 3, wherein the tension shaft includes a head arranged at a first end of the tension shaft and a nut arranged at a second end of the tension shaft, the head being located adjacent a first surface of the body and the nut being arranged adjacent a second, opposite side of the body.

5. The nasal dilator of claim 4, wherein a first through opening is formed in the first leg and a second through opening is formed in the second leg and the tension shaft extends through both the first through opening and the second opening.

6. The nasal dilator of claim 5, wherein the second through opening is threaded.

7. The nasal dilator of claim 1, wherein at least one of the first leg and the second leg is formed from a high flexure material.

8. The nasal dilator of claim 1, wherein the connecting member is formed from a medium flexure material.

9. The nasal dilator of claim 1, wherein the first leg, the second leg, and the connecting member are integrally formed.

10. The nasal dilator of claim 1, wherein at least one of the contact region of the first and second legs includes a contoured surface for gripping a nasal surface.

11. The nasal dilator of claim 10, wherein each of the contact region of the first and second legs is formed by a pad mounted to a distal end of the first leg and the second leg, respectively.

12. The nasal dilator of claim 1, wherein the first and second legs in combination with the connecting member form a body, wherein at least a portion of the body is coated with a layer of soft material.

13. The nasal dilator of claim 1, wherein the contact region of the first and second legs each includes at least one gripping feature configured to contact the interior surface of the nostril.

14. A nasal dilator comprising:
   a first leg and a second leg insertable into a pair of respective nasal openings, the first leg and the second leg each having a first end and a second end an outwardly facing surface of each of the first end of the first and second legs including a contact region configured to contact an interior surface of a nostril, wherein the first leg and the second leg are movable between an extended position and a retracted position, the first leg being arranged at an angle relative to the second leg in the extended position, wherein the first leg and the second leg are integrally formed from a resilient material having a bias toward the extended position;
a connecting member connected to and extending between the second ends of the first leg and the second leg such that a clearance is defined between the connecting member, the first leg, and the second leg; and
an adjustment mechanism receivable within an opening formed adjacent to the second end of both the first leg and the second leg, wherein the adjustment mechanism includes a tension shaft that extends through the clearance and is rotatable about an axis to oppose the bias of the first and second legs towards the extended position and control an outward pressure configured to be applied to each nostril.

* * * * *